United States Patent
Huang et al.

(10) Patent No.: US 12,263,001 B2
(45) Date of Patent: Apr. 1, 2025

(54) NEURAL INTERFACE CIRCUIT FOR BIDIRECTIONAL SIGNAL TRANSMISSION

(71) Applicant: WUHAN NEURACOM TECHNOLOGY DEVELOPMENT CO., LTD., Wuhan (CN)

(72) Inventors: Li Huang, Wuhan (CN); Cheng Huang, Wuhan (CN); Kai Li, Wuhan (CN); Moutao Li, Wuhan (CN)

(73) Assignee: WUHAN NEURACOM TECHNOLOGY DEVELOPMENT CO., LTD., Wuhan (CN)

(*) Notice: Subject to any disclaimer, the term of this patent is extended or adjusted under 35 U.S.C. 154(b) by 0 days.

(21) Appl. No.: 18/765,737

(22) Filed: Jul. 8, 2024

(65) Prior Publication Data
US 2024/0358309 A1    Oct. 31, 2024

Related U.S. Application Data

(63) Continuation of application No. PCT/CN2022/127283, filed on Oct. 25, 2022.

(30) Foreign Application Priority Data

Jan. 10, 2022 (CN) ......................... 202210023507.3

(51) Int. Cl.
*A61B 5/00* (2006.01)
*A61B 5/01* (2006.01)
*A61B 5/145* (2006.01)
*A61B 5/294* (2021.01)

(52) U.S. Cl.
CPC ................................. *A61B 5/294* (2021.01)

(58) Field of Classification Search
CPC .... A61B 5/00; A61B 5/01; A61B 5/04; A61B 5/0478; A61B 5/145; A61B 5/294
See application file for complete search history.

(56) References Cited

U.S. PATENT DOCUMENTS

| | | | |
|---|---|---|---|
| 2018/0199841 A1 | 7/2018 | Yang et al. | |
| 2019/0069787 A1* | 3/2019 | Lee ..................... | A61B 5/0031 |
| 2020/0146573 A1 | 5/2020 | Rehfeldt et al. | |

(Continued)

FOREIGN PATENT DOCUMENTS

| | | |
|---|---|---|
| CN | 101248994 A | 8/2008 |
| CN | 101522256 A | 9/2009 |

(Continued)

OTHER PUBLICATIONS

First Office Action issued in counterpart Chinese Patent Application No. 202210023507.3, dated Jan. 4, 2024.

(Continued)

*Primary Examiner* — Neel D Shah
(74) *Attorney, Agent, or Firm* — Westbridge IP LLC

(57) ABSTRACT

A neural interface circuit for bidirectional signal transmission includes at least one electrode configured to collect a neural signal and receive an excitation signal. The neural interface circuit can transmit signals bidirectionally. On the one hand, neural signals can be collected through electrodes, and on the other hand, excitation signals can be received through electrodes. The excitation signals can achieve the purpose of researching or intervening treatment.

3 Claims, 2 Drawing Sheets

(56) References Cited

U.S. PATENT DOCUMENTS

2021/0101013 A1    4/2021    Patra et al.
2023/0200879 A1*  6/2023    Liu ..................... A61B 5/4848
                                                              606/34

FOREIGN PATENT DOCUMENTS

| CN | 102247137 A | 11/2011 |
|---|---|---|
| CN | 102694552 A | 9/2012 |
| CN | 104888349 A | 9/2015 |
| CN | 104922794 A | 9/2015 |
| CN | 106037723 A | 10/2016 |
| CN | 207832242 U | 9/2018 |
| CN | 110361671 A | 10/2019 |
| CN | 111555753 A | 8/2020 |
| CN | 111897248 A | 11/2020 |
| CN | 215305975 U | 12/2021 |
| CN | 114403885 A | 4/2022 |
| JP | 2006068403 A | 3/2006 |

OTHER PUBLICATIONS

International Search Report issued in corresponding PCT Application No. PCT/CN2022/127283, dated Dec. 22, 2022.
Notification to Grant Patent Right for Invention issued in counterpart Chinese Patent Application No. 202210023507.3, dated Jun. 17, 2024.
Second Office Action issued in counterpart Chinese Patent Application No. 202210023507.3, dated Mar. 29, 2024.

* cited by examiner

NEURAL INTERFACE CIRCUIT FOR BIDIRECTIONAL SIGNAL TRANSMISSION

CROSS-REFERENCE TO RELATED APPLICATIONS

This application is a continuation application of International Application No. PCT/CN2022/127283, filed on Oct. 25, 2022, which claims priority to Chinese Patent Application No. 202210023507.3, filed on Jan. 10, 2022. The disclosures of the above-mentioned applications are incorporated herein by reference in their entireties.

TECHNICAL FIELD

The present application relates to the technical field of interface circuits, and in particular to a neural interface circuit for bidirectional signal transmission.

BACKGROUND

Action potentials can be recorded through microelectrodes. Most equipment used for long-term neural recording is a microelectrode array made of rigid metal or semiconductor. Since the action potential amplitude is small, generally at the uV level, conventional neural electrode interface readout circuits often amplify to the mV level first, and then read out through ADC sampling. However, in the field of medical applications, there is not only a need for researching and analyzing output neural signals, but further a need for research of input excitation signals and intervene treatment in the future. For this expected application, an interface circuit that can support bidirectional signal transmission of the neural electrode signal output and excitation input is needed in this field.

SUMMARY

The present application relates to a neural interface circuit for bidirectional signal transmission, which can at least solve some of the defects in the related art.

The technical solutions of the present application are implemented as follows. A neural interface circuit for bidirectional signal transmission is provided, which includes at least one electrode configured to collect a neural signal and receive an excitation signal.

In an embodiment, the neural interface circuit includes at least one collection input channel and at least one excitation output channel, and the collection input channel and the excitation output channel share a same electrode.

In an embodiment, the collection input channel includes a first gating switch connected to a control module, and the control module is configured to control the first gating switch to be off or on.

In an embodiment, the collection input channel further includes a filter and an amplifier, the electrode is connected to an input end of the filter, an output end of the filter is connected to an input end of the amplifier, and an output end of the amplifier is connected to an input end of the first gating switch.

In an embodiment, the neural interface circuit further includes an operational amplifier, and an output end of the collection input channel is connected to a non-inverting input end of the operational amplifier.

In an embodiment, the neural interface circuit further includes a sampling capacitor, one end of the sampling capacitor is grounded, and another end of the sampling capacitor is connected to the non-inverting input end of the operational amplifier.

In an embodiment, the output end of the operational amplifier is connected to an analog-to-digital (AD) conversion unit.

In an embodiment, the excitation output channel includes a second gating switch, the second gating switch is connected to a control module, and the control module is configured to control the second gating switch to be off or on.

In an embodiment, the excitation output channel is further provided with a gain scaling and filtering denoising processing circuit.

In an embodiment, when there are a plurality of electrodes, some of the electrodes are configured to collect the neural signal, and some of the electrodes are configured to receive the excitation signal.

The present application has at least the following beneficial effects. The present application provides a neural interface circuit for bidirectional signal transmission, which includes at least one electrode configured to collect neural signals and receive excitation signals. In the present application, the neural interface circuit can transmit signals bidirectionally, and neural signals can be collected through the electrodes. The electrodes can further receive excitation signals, and the purpose of research or intervention treatment can be achieved through the excitation signals.

Further, the present application provides a plurality of collection input channels and a plurality of excitation output channels. The input ends of the plurality of collection input channels are connected to a plurality of electrodes in a one-to-one correspondence. Each collection input channel is connected in series with a first gating switch. The plurality of excitation output channels are connected to a plurality of collection input channels in a one-to-one correspondence. The output ends of the plurality of excitation output channels are connected to a plurality of electrodes in a one-to-one correspondence. The input end of each excitation output channel is connected to the external excitation source. A second gating switch is connected in series with each excitation output channel. The first gating switch and the second gating switch are connected to the control module, and the control module controls the first gating switch and the second gating switch to be off or on. In the above solutions, by controlling the conduction of the first gating switch, neural electrical signals can be collected, and by controlling the conduction of the second gating switch, excitation input can be performed. While supporting the front-end electrode to sample and amplify the output, when the output channel is disconnected, the electrode is supported to optionally receive an external excitation signal. The external excitation signal can be inputted with a signal of a suitable amplitude through gain scaling, and the signal is filtered and denoised synchronously.

BRIEF DESCRIPTION OF THE DRAWINGS

To more clearly illustrate technical solutions in the embodiments of the present application or the related art, the following will briefly introduce the drawings that need to be used in the description of the embodiments or the related art. Obviously, the drawings in the following description are only some embodiments of the present application. For those skilled in the art, without creative efforts, other drawings can be obtained according to these drawings.

DETAILED DESCRIPTION OF THE EMBODIMENTS

Figure 1:
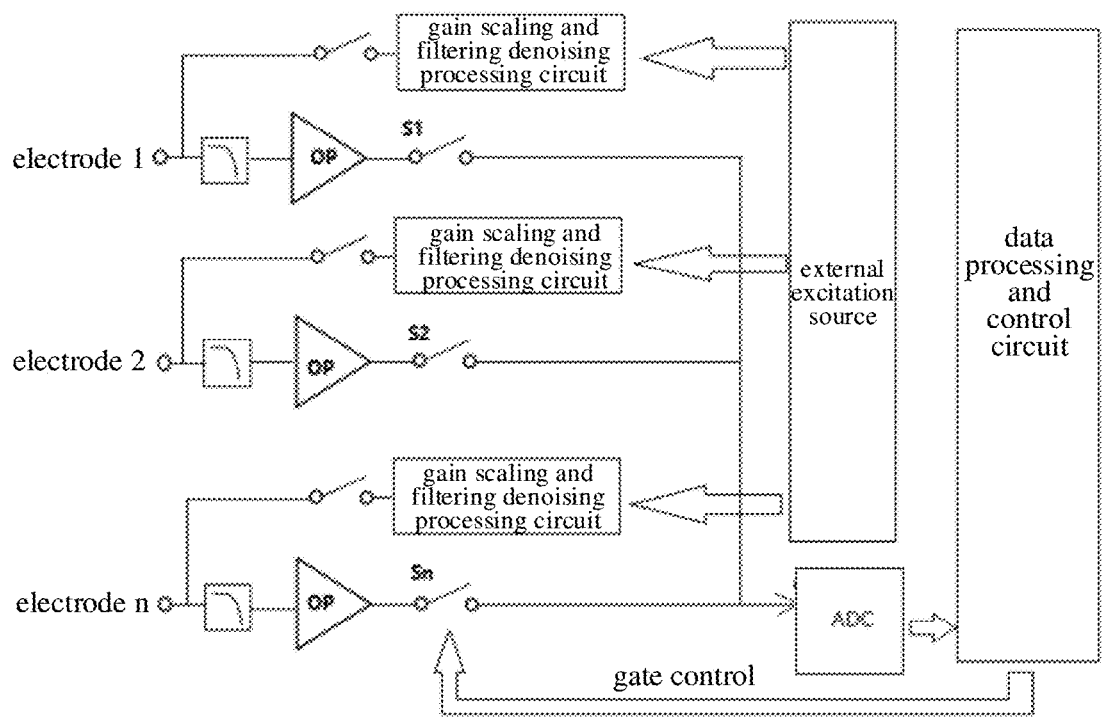
FIG. 1 is a schematic diagram of an interface circuit that can support bidirectional signal transmission of a neural electrode signal output and an excitation input according to an embodiment of the present application.

The technical solutions of the embodiments of the present application will be described in detail below with reference to the accompanying drawings. It is obvious that the embodiments described are only some rather than all of the embodiments of the present application. All other embodiments obtained by those skilled in the art based on the embodiments of the present application without creative efforts shall fall within the claimed scope of the present application.

In the description of the present application, unless otherwise stated, the terms "plurality" and "multiple" mean two or more.

First Embodiment

This embodiment provides a neural interface circuit for bidirectional signal transmission, including at least one electrode configured to collect a neural signal and receive an excitation signal. The electrode is an electrode solder point on the neural interface circuit, which is connected to an electrode point implanted in the neural cell to obtain the neural signals collected at the electrode point, and is further configured to output excitation signals to the electrode point to excite neural cells.

In an embodiment, the neural interface circuit includes at least one collection input channel and at least one excitation output channel, and the collection input channel and the excitation output channel share the same electrode. The collection input channel is configured to transmit the signals collected by the electrodes to the back-end circuit, and the excitation output channel is configured to receive the excitation signals and transmit the excitation signals to the electrodes.

In a specific application scenario, the neural interface circuit includes at least one sampling unit, and each sampling unit includes at least one collection input channel and at least one excitation output channel.

In this embodiment, the collection input channel includes a first gating switch. The first gating switch is connected to a control module, and the control module controls the first gating switch to be off or on, to selectively conduct the collection input channel.

Further, the collection input channel further includes a filter and an amplifier. The electrode is connected to the input end of the filter, the output end of the filter is connected to the input end of the amplifier, and the output end of the amplifier is connected to the input end of the first gating switch.

The neural interface circuit further includes an operational amplifier, and the output end of the collection input channel is connected to the non-inverting input end of the operational amplifier. The neural interface circuit further includes a sampling capacitor, one end of the sampling capacitor is grounded, and the other end of the sampling capacitor is connected to the non-inverting input end of the operational amplifier.

In actual application scenarios, the output end of the operational amplifier is connected to an analog-to-digital (AD) conversion unit, and the AD conversion unit is configured to convert analog signals into digital signals.

The excitation output channel includes a second gating switch. The second gating switch is connected to a control module. The control module controls the second gating switch to be off or on, to selectively conduct the excitation output channel.

In an embodiment, the excitation output channel is further provided with a gain scaling and filtering denoising processing circuit to amplify or reduce the excitation signal, and to filter and denoise the excitation signal.

In the foregoing embodiments, the same electrode has both the collection function and the excitation output function, and the electrode works in a time-sharing manner to realize the aforementioned two functions.

In an embodiment, when there are a plurality of electrodes, some of the electrodes are configured to collect neural signals, and some of the electrodes are configured to receive excitation signals, that is, the same electrode only has the collection function or the excitation output function. When a certain electrode is configured to collect neural signals, the electrode is connected to the collection input channel, and when a certain electrode is configured to receive excitation signals, the electrode is connected to the excitation output channel.

Second Embodiment

Figure 2:
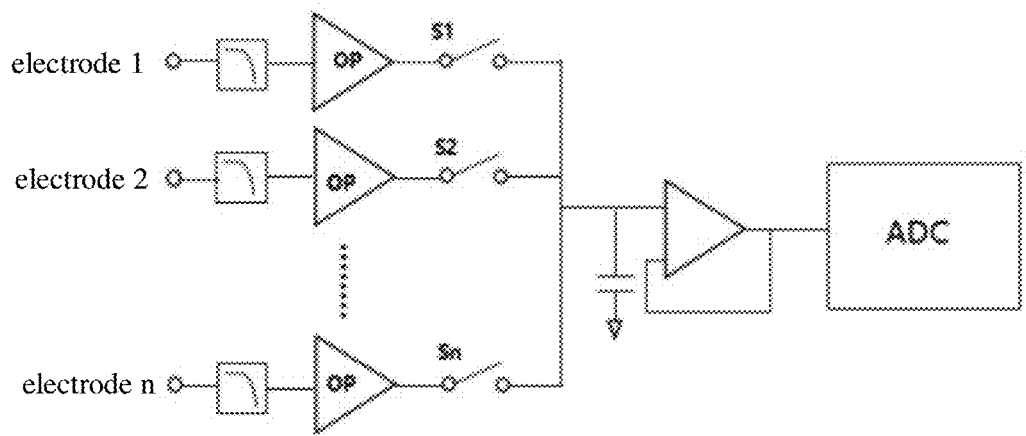
FIG. 2 is a schematic diagram of a single multi-channel sampling unit according to an embodiment of the present application.
Figure 3:
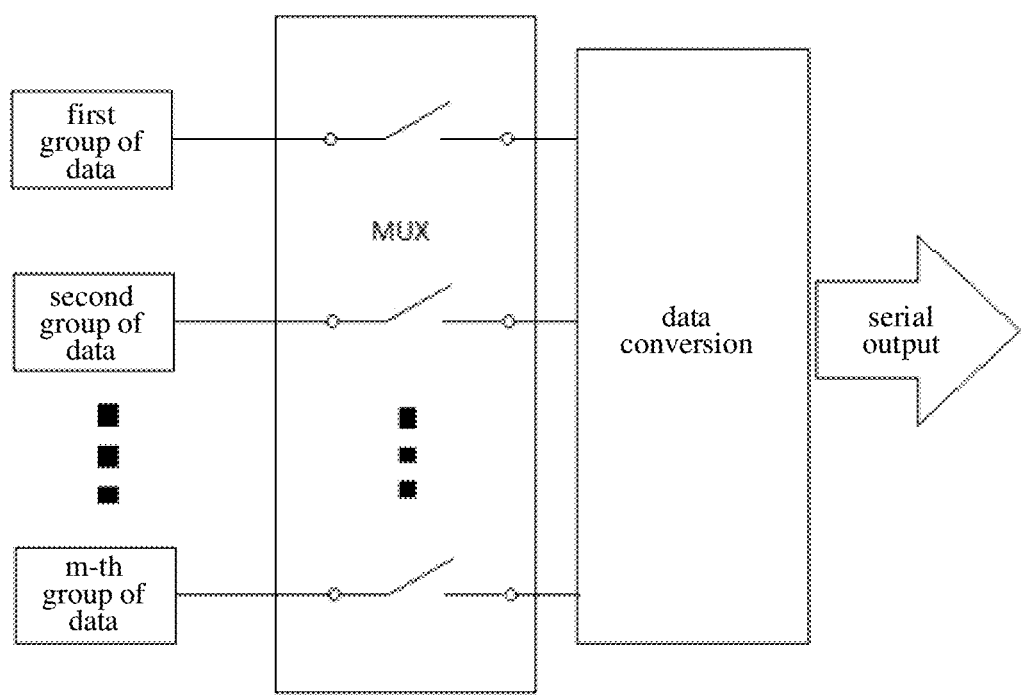
FIG. 3 is a schematic diagram of an output unit according to an embodiment of the present application.

As shown in FIG. 1 to FIG. 3, the present application discloses a neural interface circuit for bidirectional signal transmission, which includes a control module, at least one sampling unit and an output unit. The sampling unit is connected to the control module, and includes at least one collection input channel and at least one excitation output channel. The plurality of input ends of the sampling unit (namely, the input ends of a plurality of collection input channels) are respectively connected to a plurality of electrodes in one-to-one correspondence. Each collection input channel is connected in series with a first gating switch. The plurality of excitation output channels are connected to a plurality of collection input channels in a one-to-one correspondence. The output ends of the plurality of excitation output channels are connected to a plurality of electrodes in a one-to-one correspondence. The input end of each excitation output channel is connected to the external excitation source. A second gating switch is connected in series with each excitation output channel. The first gating switch and the second gating switch are connected to the control module, and the control module controls the first gating switch and the second gating switch to be off or on.

The control module of the present application is used for data processing and output control. The control module of the present application can be the microcontroller unit (MCU), but is of course not limited to MCU. The first gating switch and the second gating switch of the present application can both use a multiplexer (MUX). Of course, a relay or the like can further be used.

As one implementation method, for a large array of thousands to tens of thousands of neural electrodes, m sampling units are stacked, each sampling unit is connected to n electrodes, and the total number of electrodes is m*n. The circuit of a single sampling unit is as shown in FIG. 2.

If the single-point sampling frequency of the neural electrode is designed to be 20 KHz, the n electrodes of each sampling unit collect the neural electrical signals and then filter and amplify them. The first gating switches S1~Sn of each sampling unit are turned on in sequence for sampling, and the sampling frequency is 20 KHz. The sampled signal is converted by AD to obtain the final digital data. This is the sampling process of a multi-channel sampling unit. The present application adopts the above-mentioned sampling scheme to solve the technical problems of excessive sampling speed, high design difficulty and easy signal distortion when the conventional scheme is applied to an electrode array of tens of thousands of points.

As one embodiment, the neural interface circuit includes a sampling capacitor, the output end of the collection input channel is connected to one end of the sampling capacitor, and the other end of the sampling capacitor is grounded.

As one embodiment, the neural interface circuit further includes an operational amplifier. The output end of the collection input channel is respectively connected to one end of the sampling capacitor and the non-inverting input end of the operational amplifier. The inverting input end of the operational amplifier is connected to the output end of the operational amplifier. The output end of the operational amplifier is connected to the AD conversion module. The sampling circuit of the present application is not limited to the above embodiments, and all sampling circuits that meet the sampling requirements of the present application can be used in the present application.

Further, each collection input channel is further provided with a first signal processing unit, and the first signal processing unit and the gating switch of each collection input channel are connected in series. The first signal processing unit of this embodiment is provided in front of the gating switch. Of course, the first signal processing unit can further be provided behind the gating switch.

Further, the first signal processing unit includes a filter circuit and an amplification circuit, and the filter circuit and the amplification circuit are connected in series. The filter circuit of this embodiment is provided in front of the amplification circuit. Of course, the filter circuit can further be provided behind the amplification circuit.

Furthermore, each excitation output channel is further provided with a second signal processing unit, and the second signal processing unit of each excitation output channel is connected in series with the second gating switch.

Further, the second signal processing unit includes a gain scaling and filtering denoising processing circuit. The gain scaling and filtering denoising processing circuit of the present application can use existing excitation signal processing circuits, which will not be repeated here.

Third Embodiment

Compared with the solution in the first embodiment in which the first signal processing units are connected in series to each collection input channel of each sampling unit, each sampling unit in this embodiment is provided with only one first signal processing unit. The specific solution can be: each sampling unit further includes a first signal processing unit, the first signal processing unit is provided between the output end of the collection input channel and the sampling circuit, and the first signal processing unit is connected in series with the sampling circuit. Other technical features of this embodiment are the same as those of the first embodiment.

Fourth Embodiment

In this embodiment, an output unit is provided between the output end of each sampling unit and the control module. The structure of the output unit is as shown in FIG. 3. The output unit includes a parallel-to-serial conversion module and a plurality of sampling output channels. The input ends of a plurality of sampling output channels are connected to the output ends of a plurality of sampling units in a one-to-one correspondence, the output ends of a plurality of sampling output channels are connected to the input ends of the parallel-to-serial conversion module, and the output ends of the parallel-to-serial conversion modules are connected to the control module. Each sampling output channel is connected in series with a third gating switch. The third gating switch is connected to the control module, and the control module controls the third gating switch to be off or on.

The third gating switch of the present application can be a MUX. Of course, a relay or the like can further be used.

As one of the implementation methods, the output ends of a plurality of collection input channels are connected to the plurality of input ends of the AD conversion module in a one-to-one correspondence, and the plurality of output ends of the AD conversion module are connected to the input ends of the plurality of sampling output channels in one-to-one correspondence.

The present application is aimed at large arrays with thousands to tens of thousands of neural electrodes. The circuit can be divided into m sampling units, each sampling unit includes n electrodes, each sampling unit has n collection input channels, and the total number of electrodes is =m*n. During sampling, m*n electrodes collect neural electrical signals to control the gating switches S1~Sn of each sampling unit to be turned on in sequence, sampling is performed through the collection input channel, then the sampled signal is converted through AD to obtain final digital data. The m sampling units work simultaneously and output m data. By controlling the on-off state of the third gating switch of each sampling output channel, each data can be switched and outputted, and parallel-to-serial conversion can be performed on the outputted data through the parallel-to-serial conversion module. In this way, not only the data output rate can be reduced, but further the overall power consumption can be reduced.

The interface circuit of the present application that can support bidirectional signal transmission of the neural electrode signal input and excitation output can be used in, but is not limited to, fields including cranial neurals, visual neurals, and motor neurals. While supporting the front-end electrode to sample and amplify the output, when the output is disconnected, the single-point electrode is supported to optionally receive an external excitation signal. The external excitation signal can be inputted with a signal of a suitable amplitude through gain scaling, and the signal is filtered and denoised synchronously.

The above are only some embodiments of the present application, and do not limit the scope of the present application. Under the concept of the present application, modifications, equivalent substitutions, improvements, etc., shall fall within the claimed scope of the present application.

What is claimed is:

1. A neural interface circuit for bidirectional signal transmission, comprising:
   a plurality of electrodes configured to collect a neural signal and receive an excitation signal;
   a plurality of sampling units, wherein each sampling unit comprises a plurality of collection input channels and a plurality of excitation output channels, the plurality of excitation output channels correspond to the plurality of collection input channels one by one, a collection input channel and a corresponding excitation output channel share a same electrode, the collection input channel is provided with a first gating switch, the first gating switch is connected to a control module, the control module is configured to control the first gating switch to be off or on to conduct the collection input channel; the excitation output channel comprises a second gating switch, the second gating switch is connected to the control module, the control module is configured to control the second gating switch be off or on to selectively conduct the excitation output channel; wherein each collection input channel is further provided with a first signal processing unit, the first signal processing unit comprises a filtering circuit and an amplifying circuit, the filtering circuit is connected in series with the amplifying circuit; and the excitation output channel is further provided with a gain scaling and filtering denoising processing circuit;

an operational amplifier, wherein an output end of the collection input channel is connected to a non-inverting input end of the operational amplifier, an inverting input end of the operational amplifier is connected to an output end of the operational amplifier, and the output end of the operational amplifier is connected to an analog-to-digital (AD) conversion unit;

a sampling capacitor, wherein one end of the sampling capacitor is grounded, and another end of the sampling capacitor is connected to the non-inverting input end of the operational amplifier;

an output unit, wherein the output unit comprises a parallel-to-serial conversion module and a plurality of sampling output channels, input ends of the plurality of sampling output channels are connected to output ends of the plurality of sampling units in a one-to-one correspondence, output ends of the plurality of sampling output channels are connected to an input end of the parallel-to-serial conversion module, an output end of the parallel-to-serial conversion module is connected to the control module, each sampling output channel is connected in series with a third gating switch, the third gating switch is connected to the control module, and the control module is configured to control the third gating switch to be off or on; and m sampling units disposed in a stacked manner, wherein each sampling unit is connected to n electrodes, there are m*n electrodes, m*n electrodes are configured to collect neural electrical signals to control the first gating switches S1~Sn of each sampling unit to be conducted in sequence during sampling, the acquisition input channel is configured for sampling, and a sampled signal is converted into final digital data through AD conversion; m sampling units work simultaneously and output m data; each data is switched to output by controlling the third gating switch of each sampling output channel to be off or on, and a parallel-to-serial conversion is performed on the output data through a parallel-to-serial conversion module.

2. The neural interface circuit according to claim 1, wherein the first signal processing unit of each acquisition input channel is connected in series with the first gating switch of each acquisition input channel.

3. The neural interface circuit according to claim 1, wherein some electrodes are configured to collect the neural signal, and some electrodes are configured to receive the excitation signal.

* * * * *